United States Patent
Kwok et al.

(10) Patent No.: US 8,051,850 B2
(45) Date of Patent: Nov. 8, 2011

(54) NASAL DILATOR

(75) Inventors: Rodney Philip Kwok, Chatswood (AU); Ron Richard, Temecula, CA (US)

(73) Assignee: ResMed Limited, Bella Vista (AU)

( * ) Notice: Subject to any disclaimer, the term of this patent is extended or adjusted under 35 U.S.C. 154(b) by 754 days.

(21) Appl. No.: 11/886,677

(22) PCT Filed: Mar. 10, 2006

(86) PCT No.: PCT/AU2006/000321
§ 371 (c)(1),
(2), (4) Date: Sep. 19, 2007

(87) PCT Pub. No.: WO2006/099658
PCT Pub. Date: Sep. 28, 2006

(65) Prior Publication Data
US 2009/0183734 A1    Jul. 23, 2009

Related U.S. Application Data

(60) Provisional application No. 60/663,725, filed on Mar. 22, 2005.

(51) Int. Cl.
*A61M 15/00* (2006.01)
(52) U.S. Cl. .............. 128/200.24; 606/194; 600/593
(58) Field of Classification Search ........... 128/200.24, 128/204.23; 606/199; 600/587
See application file for complete search history.

(56) References Cited

U.S. PATENT DOCUMENTS

| | | | |
|---|---|---|---|
| 5,546,929 A | 8/1996 | Muchin | |
| 5,611,334 A * | 3/1997 | Muchin | 128/200.24 |
| 6,228,101 B1 | 5/2001 | Stratton | |
| 6,336,456 B1 * | 1/2002 | Ruben | 128/206.19 |
| 6,453,901 B1 | 9/2002 | Ierulli | |
| 6,470,883 B1 * | 10/2002 | Beaudry | 128/200.24 |
| 6,663,649 B2 | 12/2003 | Stratton | |
| 6,860,263 B1 * | 3/2005 | Scoggins | 128/200.24 |
| 7,114,497 B2 * | 10/2006 | Aylsworth et al. | 128/204.18 |
| 7,178,525 B2 * | 2/2007 | Matula et al. | 128/206.27 |
| 2001/0023695 A1 | 9/2001 | Auriemma | |
| 2005/0027230 A1 * | 2/2005 | Beaudry | 602/54 |
| 2005/0199242 A1 * | 9/2005 | Matula et al. | 128/207.13 |
| 2009/0000616 A9 * | 1/2009 | Fenton | 128/200.24 |

FOREIGN PATENT DOCUMENTS

| | | |
|---|---|---|
| WO | 98/27897 | 7/1998 |
| WO | 98/37924 | 9/1998 |
| WO | 01/60294 A1 | 8/2001 |

OTHER PUBLICATIONS

International Search Report for International Patent Application No. PCT/AU2006/000321 mailed Jun. 6, 2006.

* cited by examiner

*Primary Examiner* — Max Hindenburg
*Assistant Examiner* — Renee Danega
(74) *Attorney, Agent, or Firm* — Nixon & Vanderhye P.C.

(57) ABSTRACT

A nasal dilator includes a contact pad attachable to a user's facial region below the user's eye and outboard from the user's nose. A tugging device is coupled with the contact pad and urges the contact pad in a direction away from the user's nose. With this structure, effective dilation of the nasal passages can be achieved in a comfortable manner. The dilator may also be incorporated into a CPAP mask and/or form part of an automated control system.

12 Claims, 7 Drawing Sheets

NASAL DILATOR

CROSS-REFERENCES TO RELATED APPLICATIONS

This application is the U.S. national phase of International Application No. PCT/AU2006/000321, filed Mar. 10, 2006, which designated the U.S. and claims priority to U.S. Provisional Application No. 60/663,725, filed Mar. 22, 2005, the entire contents of each of which are hereby incorporated by reference.

STATEMENT REGARDING FEDERALLY SPONSORED RESEARCH OR DEVELOPMENT (Not Applicable)

BACKGROUND OF THE INVENTION

The present invention relates to a nasal dilator and, more particularly, to an outboard nasal dilator and mask-integrated nasal dilator for reducing nasal airway resistance.

Nasal airway resistance causes an increased breathing effort and also promotes mouth breathing. Nasal breathing is preferable in most day-to-day circumstances because the nose provides a means to filter incoming air by trapping atmospheric pollutants in the nasal passage hairs and inner nostril mucosa (sticky) membrane before the air enters the lungs. The nasal passages also provide a means to warm and moisturize incoming air to provide breathing comfort. Increased nasal resistance can deprive patients of air and oxygen.

Where nasal positive airway therapy devices are used such as with continuous positive airway pressure (CPAP) or other non-invasive positive pressure ventilation (NIPPV) devices to treat patients with Obstructive Sleep Apnea (OSA), an increase in nasal flow resistance will affect therapy by increasing work of breathing and by increasing pressure swings. Swings reflect the variation in pressure that the patient experiences when breathing; the lower the swings, the more comfortable it is to breathe by the patient. Nasal resistance has been well documented to negatively impact the effectiveness of CPAP therapy and patient compliance. Many people suffer from seasonal allergies and congestion due to upper respiratory problems associated with colds, flu or rhinitis. Based on Poiseuilles Law, one can clearly see the impact resistance has on pressure and flow curves. If the main conduit for CPAP is via the nasal passage, and resistance changes by even a small amount, the effective pressure delivered to the patient's airway is potentially compromised and could result in sub-therapeutic pressures being delivered to the patient. A commonly recognized phenomenon during REM sleep is phasic nasal breathing whereby the turbinates rest, and breathing flow gradually switches from one nare to the other during the night. In some patients this could have a significant effect on their apnea/hypopnea index (AHI) during the most vulnerable period of sleep.

The nasal passage region that is most likely to create airflow resistance is around the region known as the nasal vents. This is where the cross-sectional area of the nasal passage is narrowest and also susceptible to narrowing. The nasal vents coincide with a region in the soft-tissue nasal passages that is approximately just below the nasal bone on either side if the nose (or nasal bridge). Current art such as the "Breathe-Right™" nasal strips intend to open the nasal passages in the nasal vent region.

There are other types of devices that are attached to the sides of the nose. One such device is a nasal dilator that does not fit over the bridge of the nose but is attached to each side of the nose by self-adhesive tape. See, for example, U.S. Pat. No. 6,228,101 and U.S. Pat. No. 6,663,649.

Numerous devices and current art assist to reduce nasal resistance in the nasal vent region and physically and mechanically cause the nasal passages to dilate or open further in their internal cross-sectional area. These nasal dilator mechanical devices assist in soft-tissue dilation by splinting the nasal passages open further either internally, e.g., by way of outwardly tensioned springs, to external devices as previously mentioned that are attached to the outside surface of the nose by adhesive or by some other mechanical fastener.

The problem with current art is that they do not recognize that the exterior and interior of the nose is sensitive to contact and also contact pressure. For example, the interior of the nose contains nasal hairs and soft-tissue membranes that are sensitive to being brushed against with physical devices.

Also considering the exterior of the nose, devices that attach by adhesives or self-adhesives are not ideal as the adhesives are designed to be a compromise on a secure fit and the ability to remove them easily from the skin after use. The skin surface on the nose is particularly sensitive to touch and generally more so than the surrounding exterior surfaces on the face or head.

Any nasal dilator and any mechanical contact with the nose (internally or externally) may cause irritation to a patient.

A further disadvantage of current art devices is their inability to be combined or integrated into a nasal mask system when the patient is prescribed with a mask interface such as when used with positive airway pressure therapy such as CPAP. It would provide great user convenience for mask wearers to minimize the number of operations or steps required to have both nasal dilation and proper fit of a mask interface.

Current art requires a cumbersome initial installation of the nasal dilator and subsequently the mask interface. Other designs utilize tensioning springs that sit over the nose, which may also interfere with the nasal mask interface. Furthermore, any material that rests between the sealing surface of a nasal mask cushion seal and the face may affect sealing performance of the mask and thereby affect treatment.

BRIEF SUMMARY OF THE INVENTION

The invention aims to ameliorate one or more of the above problems by a novel idea for a device that reduces flow impedance within a breathing patient's airway (nose). By reducing impedance, breathing resistance is therefore reduced and breathing comfort and patient compliance improves.

It is an aspect of the invention to provide a mechanical dilator that substantially fastens to a region outboard of the nose region (i.e., not to the nose), but still mechanically affects the dilation of the nasal passages (nasal vents).

It is another aspect of the invention to combine a nasal dilator with a current nasal mask that is integrated or removably integrated into the mask interface.

Improved breathing comfort results in patients improving their lung function exchange, which can offer benefits from improving a sportsperson's performance through improved oxygenation through to improving therapy when used in conjunction with medical ventilation devices. For example, when used with CPAP therapy, embodiments of the invention can provide improved breathing comfort and/or improved therapy, resulting in good patient compliance to treatment.

A dilator according to an aspect of the invention acts upon the nasal passages whilst not physically attached to the sensitive nose exterior and/or the nasal passages. In one embodiment, the dilator acts (and contacts) upon the region of the face, more specifically the cheeks (generally in the region of the cheekbones a short distance below the eyes) adjacent the nose. The nasal dilator moves the skin layer and somewhat the underlying soft tissue in an outwards or generally sideways direction, preferably toward the user's ears.

As the soft tissue is subsequently continuously formed as a facial feature (common soft tissue layer from cheek to nose tip), moving the facial tissue outwardly will subsequently act upon the sides of the nose. As the sides of the nose form a common wall to the nasal vent (narrow section of the nasal passages), the nasal vent is subsequently also drawn in a sideways direction thus maintaining or increasing the nasal vent cross-sectional area to reduce flow impedance and increase airflow into the patient's airway.

In an exemplary embodiment of the invention, a nasal dilator includes a contact pad attachable to a user's facial region below the user's eye and outboard from the user's nose; and a tugging device coupled with the contact pad, where the tugging device urges the contact pad in a direction away from the user's nose. The contact pad may include one of an adhesive, a self-adhesive tape, and/or a friction surface on a side thereof facing the user. The contact pad may be formed of a gel material. In one arrangement, the tugging device is composed of a strip of flexible material attached at a first end thereof to the contact pad and attached at a second end thereof to a securing device, which securing device is fixable relative to the user such that the flexible strip is placed under tension. In this context, the securing device may be an adhesive pad attachable to the user's face or a head strap or the like. Preferably, an outer surface of the material strip is non-reflective, e.g., of a dark color or textured. The material strip may also be provided with text and/or graphics.

In another arrangement, the dilator includes two contact pads attachable to respective facial regions on either side of the user's nose. The tugging device urges both contact pads in directions away from the user's nose. In this context, the tugging device may be an adjustable head strap. Alternatively, the tugging device may be an outward biased U-shaped spring, where the contact pads are secured to opposite ends of the spring. In this arrangement, the contact pads may be a self-adhesive layer on a side thereof facing the user, or alternatively may be a friction surface on a side thereof facing the user. A head strap may fit over the spring on the user's face.

In another exemplary embodiment of the invention, the nasal dilator is combined with a mask of a CPAP system. In this context, the mask includes a mask cushion, and the nasal dilator is preferably built into the mask cushion. Moreover, the nasal dilator may include two contact pads attachable to respective facial regions on either side of the user's nose, where the tugging device is attached to the mask cushion such that when in use the tugging device urges both contact pads in directions away from the user's nose. The tugging device may be an adjustable spring member.

The nasal dilator of embodiments of the invention may also be combined with a nasal pillow system, where the nasal dilator is attached to the nasal pillow frame.

In yet another exemplary embodiment of the invention, a nasal dilator system incorporates the nasal dilator noted above and a nasal resistance measuring device. A control system receives output from the nasal resistance measuring device, and a force adjustment mechanism adjusts the force applied by the tugging device based on the output from the nasal resistance measuring device. The force adjustment mechanism may be a motor. With two contact pads, the force adjustment mechanism can effect independent adjustment of the force on each of the contact pads, which independent adjustment may be dependent on a position of the user or the output from the nasal resistance measuring device. This independent adjustment accommodates variable side-to-side dilation based on patient need, e.g., due to nasal cycling.

In still another exemplary embodiment of the invention, a method of reducing nasal resistance includes the steps of securing a contact pad to a user's facial region below the user's eye and outboard from the user's nose; and urging the contact pad in a direction away from the user's nose with an urging force that opens the user's nasal vent. The method may additionally include measuring nasal resistance in the user's nasal passages, and adjusting the urging force based on the nasal resistance.

BRIEF DESCRIPTION OF THE DRAWINGS

These and other aspects and advantages of the present invention will be described in detail with reference to the accompanying drawings, in which.

DETAILED DESCRIPTION OF PREFERRED EMBODIMENTS

Independent Nasal Dilator—Flexible Strip Attachment

Figure 1:
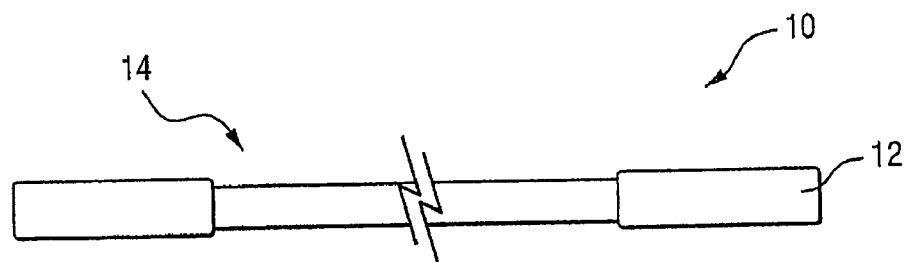
FIG. 1 illustrates one embodiment of the invention showing an independent outboard nasal dilator.
Figure 2:
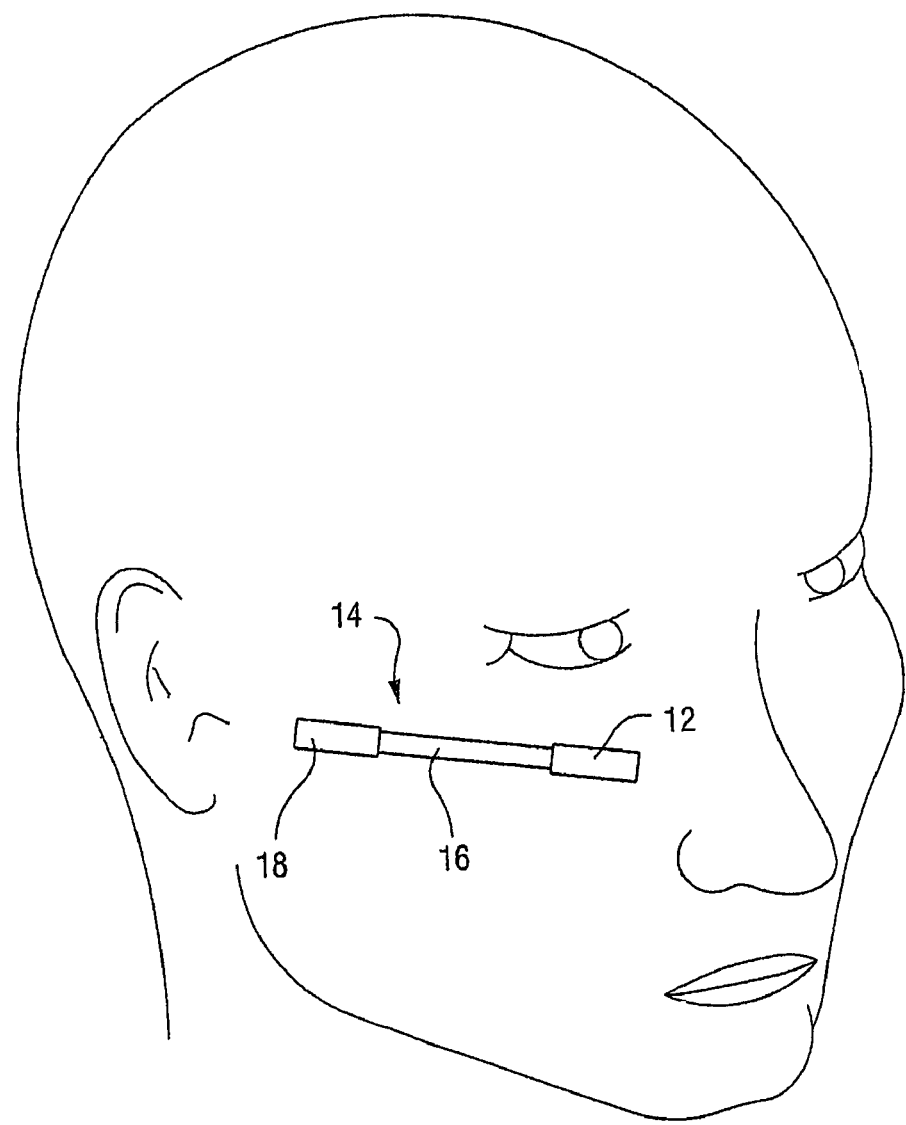
FIG. 2 shows the nasal dilator of FIG. 1 secured to a patient's face.
Figure 3:
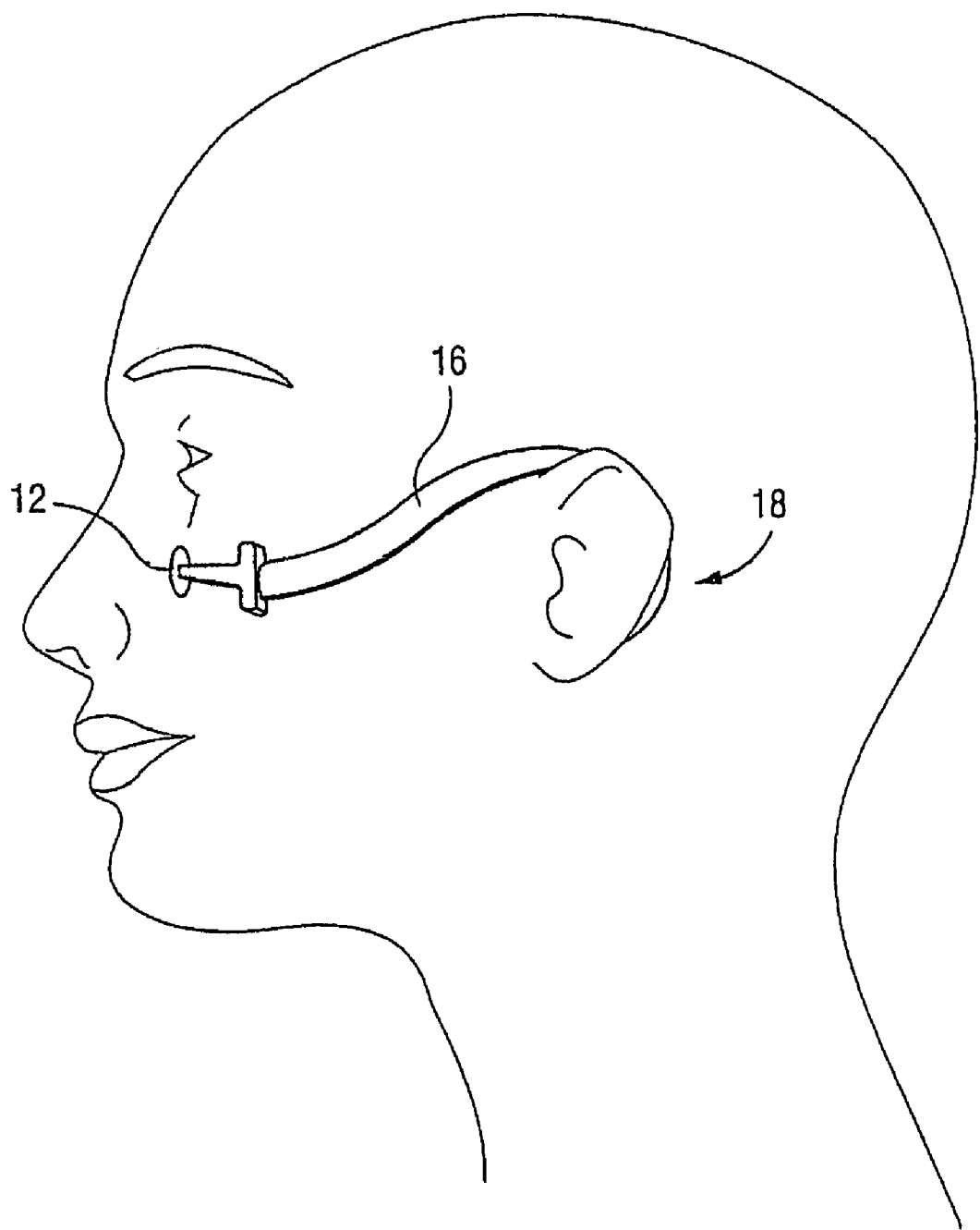
FIGS. 3 and 4 show alternative securing structures.
Figure 4:
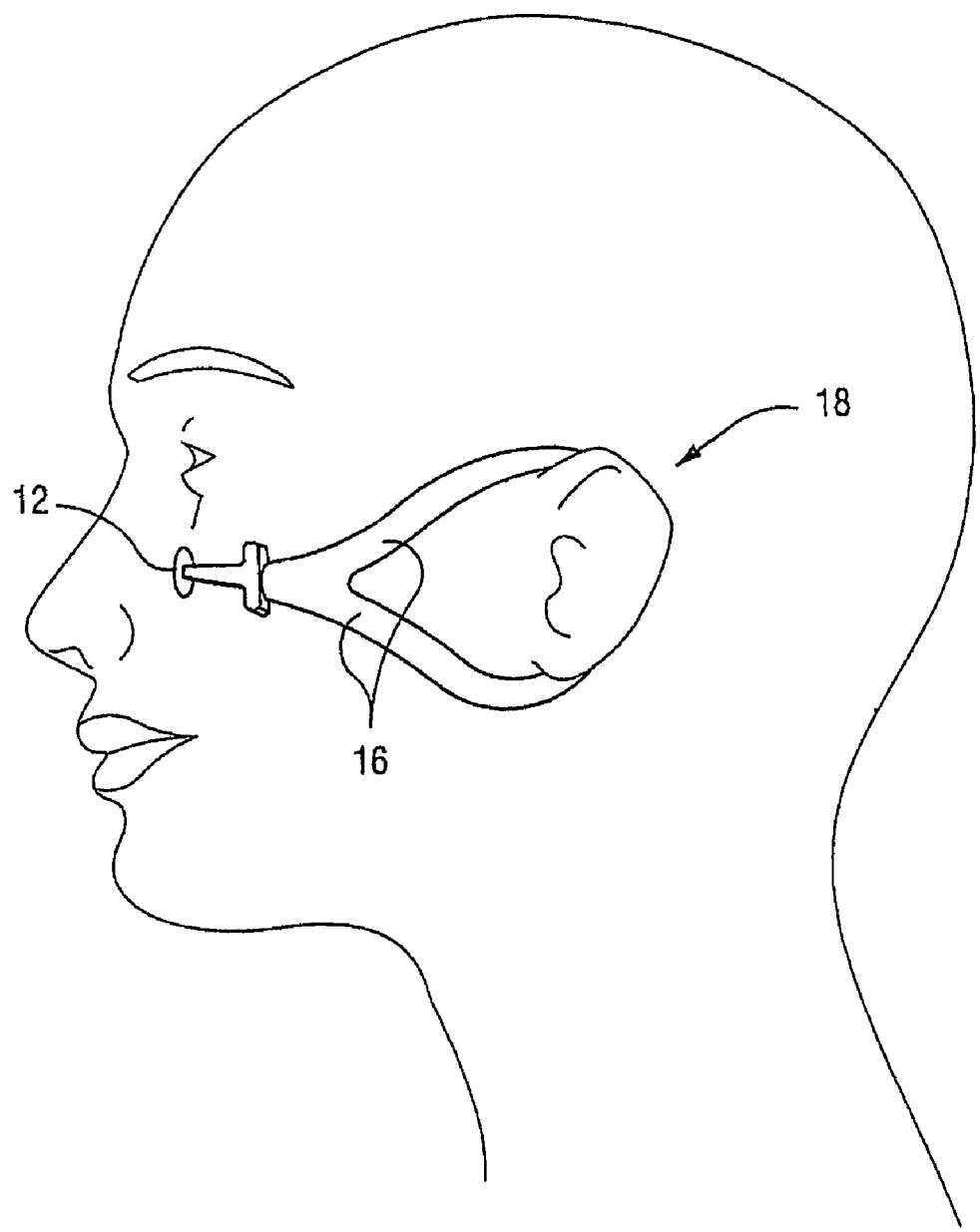

With reference to FIG. 1, in a first embodiment of the invention, a nasal dilator 10 includes at least one contact pad 12 attachable to a facial region below the user's eye and outboard from the user's nose. More particularly, the "facial region" defined according to the invention is generally any area on the skin surface overlying the bone region known as Zygomatic bone (cheekbone region). The "facial region" also encompasses anywhere between the ear and nose, and also between the infraorbital margin (eye socket) and the line of the lips/mouth/chin. A tugging device 14 is coupled with the contact pad 12 and urges the contact pad 12 in a direction away from the user's nose. As shown in FIG. 2, in this embodiment, the tugging device includes a strip of flexible material 16 attached at a first end to the contact pad 12 and attached at a second end to a securing device 18, which is fixable relative to the user such that the flexible strip 16 is placed under tension. In the embodiment shown in FIG. 2, the securing device 18 is an adhesive pad attachable to the user's face. The adhesive pad securing device 18 is pulled in tension, which dilates the nasal passages, and is attached to the face just in front of the ear as shown. In an alternative, the securing device 18 could engage behind the wearer's ear, like a pair of eye glasses, examples of which are shown in FIGS. 3 and 4.

Figure 5:
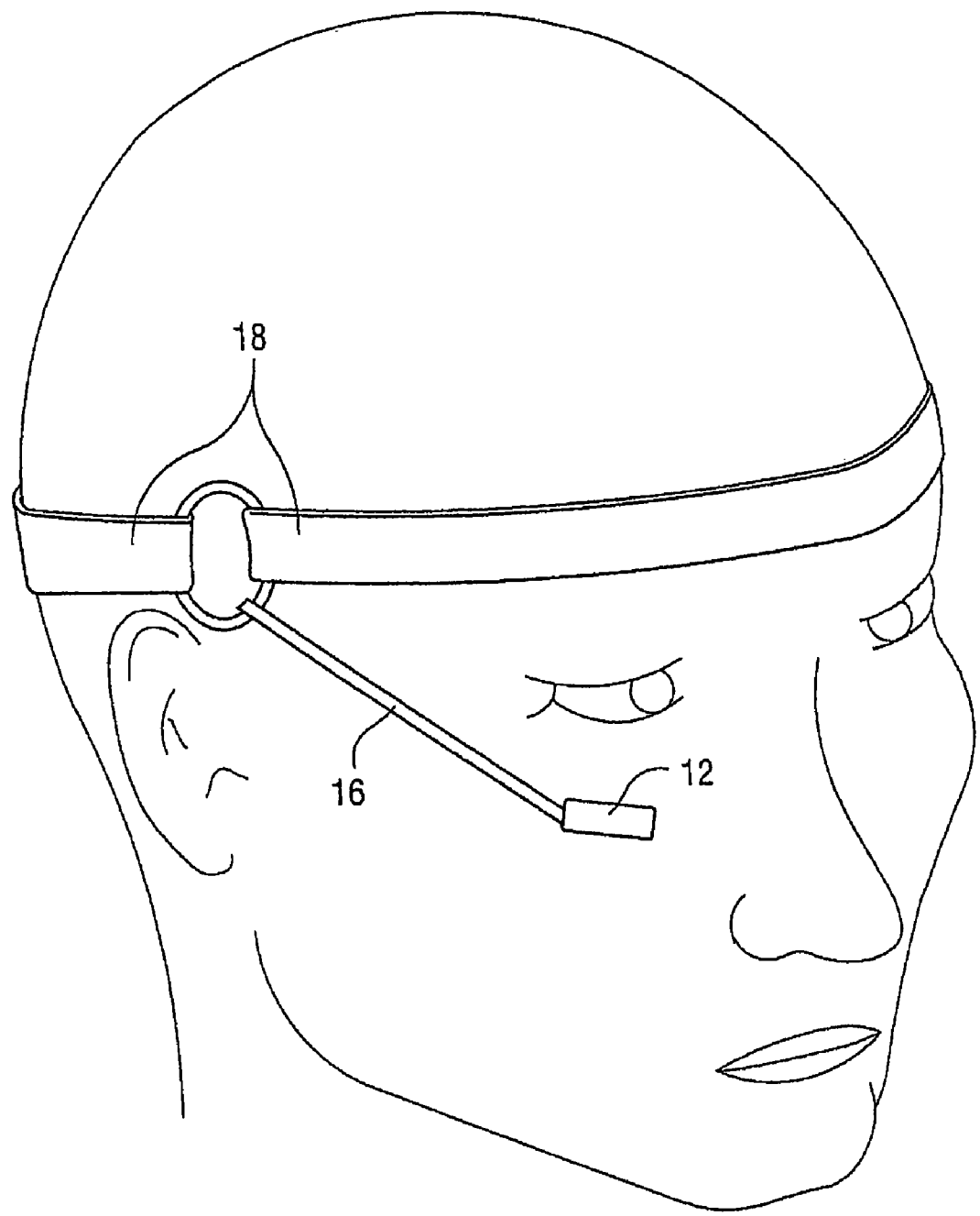
FIG. 5 shows the nasal dilator of FIG. 1 secured to the patient's face using a head strap.

FIG. 5 illustrates the use of a head strap as an alternative securing device 18. In this embodiment, the tension required to open the nasal passages is provided by a tensioning strap, preferably elastic and resilient that is attached to a pair of dilator contact pads 12 and is passed around the back of a wearer's head. By tightening the headgear strap, the dilator increases the effect.

The attachment point for the contact pad 12 to the patient's head by any mechanical means (e.g., friction pads, self-adhesive tape, adhesives) may be placed at any point or region outboard of the nose bounded by the eyes, ears, and chin. It has been discovered that drawing the soft-tissue in the cheek region below the eyes and to the side of the nose affects the nasal passages.

The flexible strip 16 is preferably relatively inelastic and does not stretch. For example, typical woven fabric, e.g. cotton, can conform to the curvature of the face being flexible but does not stretch or elongate. The dilator strip may alternatively provide a tension spring-like force. Materials used may include silicone rubber or a thermoplastic elastomer. The product may be assembled by laminations of materials, or insert molded, or co-molded (that is, more than one material molded together during manufacture). An underside of the flexible strip 16 is preferably non-adhesive with the ability to slide over the skin.

Athletes such as gridiron players are known to place black face paint or other substance that is applied like face cream to the skin beneath the eyes to minimize distracting reflections. Additionally, some players are known to wear prior art nasal strips to improve breathing through the nose. In this context, an outer surface of the flexible strip 16 may be formed with a non-reflective surface. For example, the strip 16 and/or pads may be dark colored or textured. Thus by improving breathing and reducing reflection, this embodiment of the invention provides a dual utility.

The contact pads 12 may be self-adhesive strips constructed from a number of materials. For example, self-adhesive wound dressing materials that are typically laminated adhesive on a textile carrier may be used. These pads 12 may be simply rectangular pieces or specially contoured to avoid certain facial features such as the eyes.

The dilator 10 in this embodiment may of course include combinations of materials with embodiments that include stretching and non-stretching regions to improve conformity and comfort on the face. The preferred embodiment is also very low in profile (e.g., preferably 1-5 mm or less) to avoid contact pressure should the face contact bedding materials.

Independent Nasal Dilator—Spring Attachment

Figure 6:
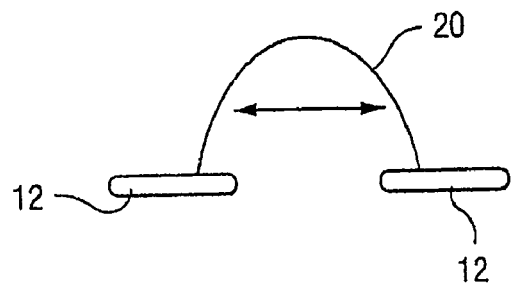
FIG. 6 shows a nasal dilator using a U-shaped spring according to an embodiment of the present invention.
Figure 7:
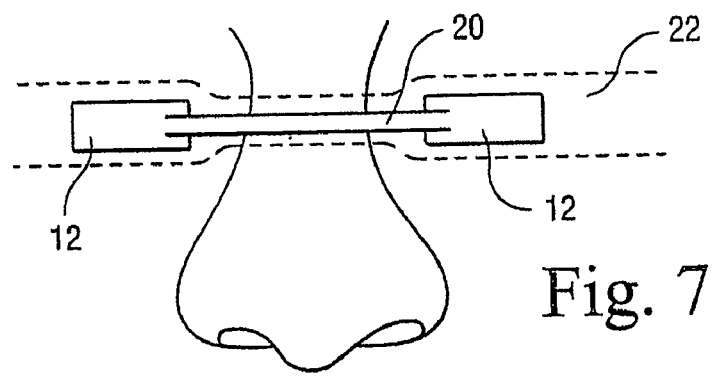
FIG. 7 shows the nasal dilator of FIG. 6 secured to a user's face.

With reference to FIGS. 6 and 7, a second embodiment of the invention utilizes a U-shaped spring 20 over the bridge of the user's nose where its ends are biased to spring outwards away from the sides of the nose (see arrows in FIG. 4). These ends may be attached to self-adhesive foam contact pads 12 that are adhered to the region outboard of the nose as previously described. The spring 20 causes the cheek regions and thus the sides of the nose to move outwards thus dilating the nasal passages.

The pads 12 may alternatively be provided with a friction quality such as textured rubber that tends to grip to the skin (e.g., soft 10 Shore A hardness silicone rubber or tacky gel). A strap 22 (shown in dashed line in FIG. 5) or other mechanical device may force the pads 12 against he face to prevent them from sliding by increasing the friction. The resultant force of the spring 20 serves to dilate the nasal passages.

Mask Version

Figure 8:
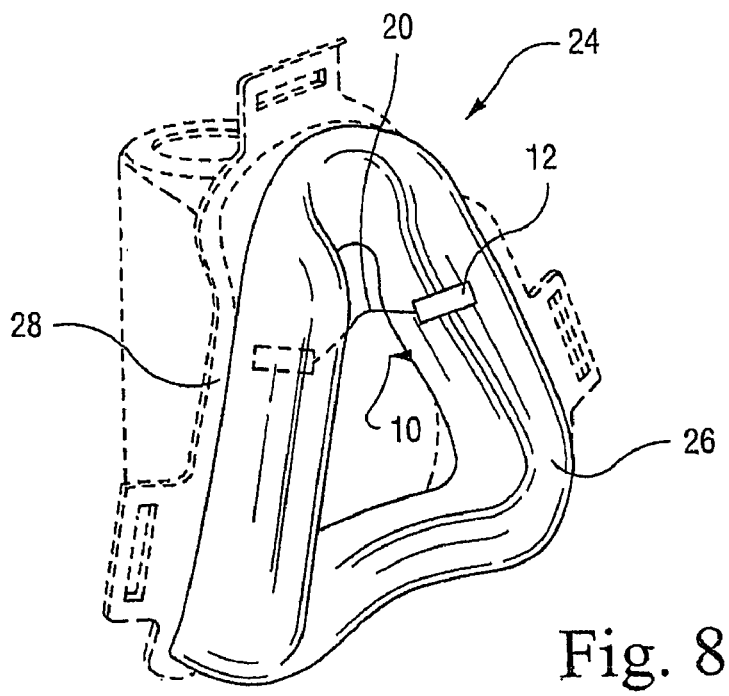
FIG. 8 is a schematic illustration of a nasal dilator built into a CPAP mask according to an embodiment of the present invention.

With reference to FIG. 8, this additional friction may also be achieved by the application of a CPAP nasal mask 24 that is seated on or supports the friction pads 12. The mask's headgear straps (not shown) secure the mask cushion 26 and therefore the friction pads 12 against the facial skin.

The dilator 10 may be secured to a mask interface either in permanent or semi-permanent assembly. The dilator 10 for example may be removable from the mask frame 28 or assembled to it. The dilator 10 may also be combined with at least one mask component, for example an over-molding process, where a mask cushion could be molded over the dilator's metal or plastic or other spring.

With continued reference to FIG. 8, the nasal dilator 10 built into the mask cushion preferably utilizes a spring-like structure, which can be attached, via disposable adhesive strips, which can then be connected to the interior of the nasal cushion as shown. The spring system 20 permits tension adjustments based on patient activation and adjustment. Simply squeezing or applying subtle pressure to form the spring tension and curvature to the patient's nasal passageways with the adhesive strip will open the nasal passages and achieve improved airflow.

Before placing the mask 24 on the face, the patient would apply the adhesive strip to the spring mechanism on the interior of the mask cushion 26. The positioning of the spring and strip on the nasal passage is preferable in terms of effectiveness and comfort. The anatomy of the patient also plays a role. Narrow or slightly obstructed nasal passages may experience the greatest benefit, but overall any improvement in flow to the nasal passages would be beneficial. This embodiment may also be used with a full-face mask, and the invention is not meant to be limited to the illustrated embodiment.

Figure 9:
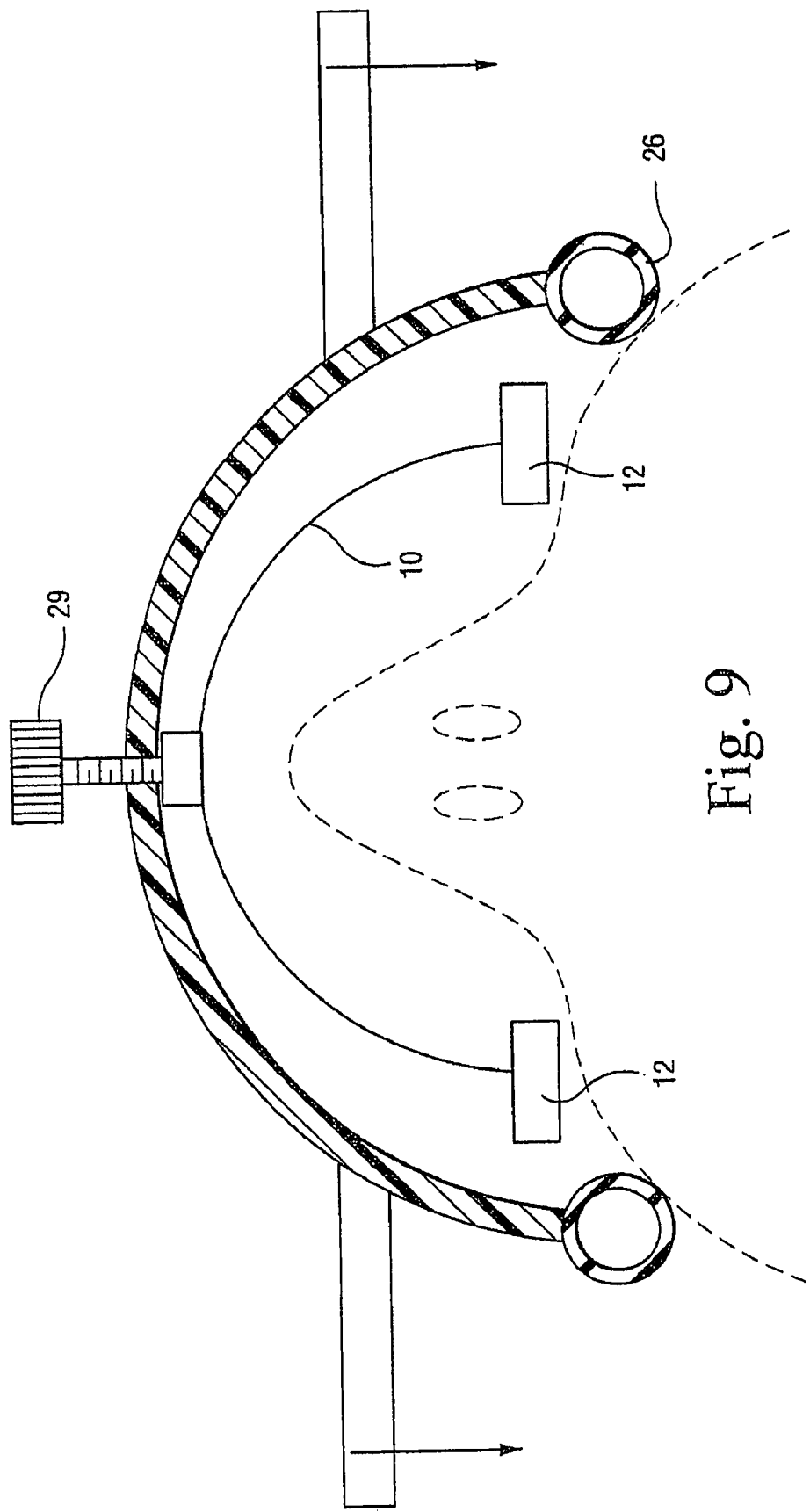
FIG. 9 shows an alternative arrangement built into a CPAP mask.

FIG. 9 illustrates an alternative arrangement. In this configuration, dilation is relative to headgear strap tension. A know 29 may also allow balancing dilation to custom fit.

Nasal Pillow Version

Figure 10:
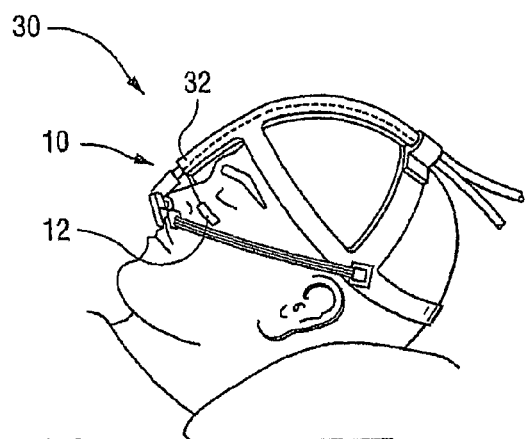
FIG. 10 shows a nasal dilator attached to a nasal pillow frame of a nasal pillow system according to an embodiment of the present invention.

With reference to FIG. 10, a conventional nasal pillow system 30 is shown attached to a patient. A simple attaching means secures the nasal dilator 10 to a nasal pillow frame 32.

Nasal Dilator System

Figure 11:
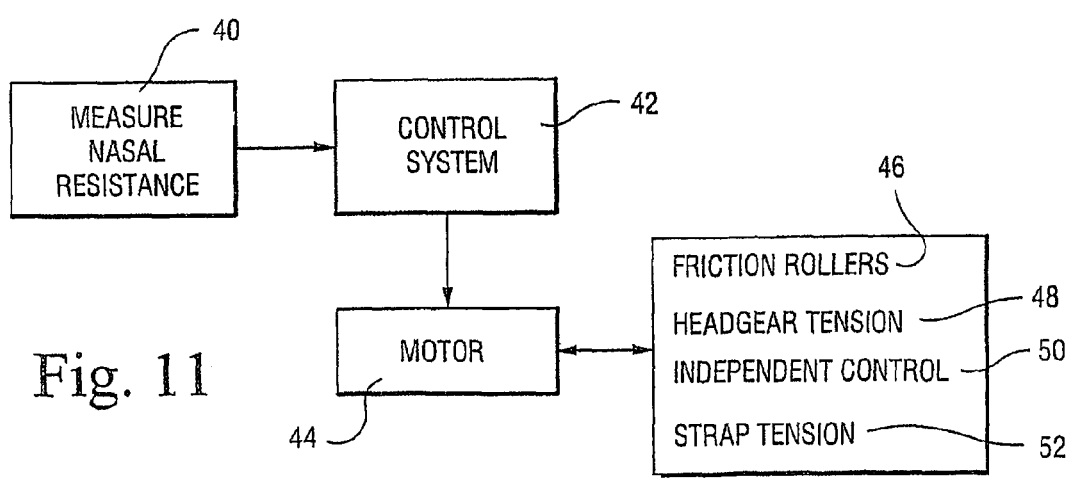
FIG. 11 is a block diagram illustrating a nasal dilator system according to an embodiment of the present invention.

Further embodiments relate to a dilator system that can react to certain conditions when used in conjunction with a patient. In some cases, these embodiments/systems may allow for minimal or no nasal dilation in response to natural "nasal cycling." FIG. 11 is a schematic block diagram of a more sophisticated system that can actively increase or decrease nasal passage flow according to patient requirements. Nasal resistance can be measured using a multitude of known devices 40, such as those utilizing hot wire resistance to measure air flow. A control system 42 receives output from the nasal resistance measuring device, and a force adjustment mechanism controls the tugging device 14 to adjust a force applied thereto based on the output from the nasal resistance measuring device 40.

A servo motor control system (e.g., an electric stepper motor control) 44 can be controlled to drive silicone rubber friction rollers 46 located outboard and on either side of the nose to dilate the nasal passage via rotation causing the soft tissue to also move outwards (to the nose) on detection of airway (nostril) impedance. This can be completely variable or provided in at least two positions. Furthermore, the headgear tension as described earlier may also be controlled using a tensioning device 48, such as an electromagnetic motor/solenoid or other tensioning device.

Note that this embodiment of the invention does not limit the type of active control and may be any type of motor control, electromagnetic, bi-metallic springs that can be heated to deflect, magnetic drives, pneumatic motors etc.

The control system 42 may alternatively or additionally react to sleeping position or nasal cycling. For example, as a patient rolls onto their left side, this may cause the left nostril to reduce in flow. The dilator may by increased tension or force maintain the nasal airflow on this side via independent control 50. The controller 42 may utilize body position sensors similar to those yaw and roll sensors found in automotive stability control systems or otherwise simply a tilt switch (mercury or conductive ball).

Furthermore, an embodiment includes a method to detect when the airflow is reduced on one side and actively dilate the corresponding side. As variations can occur during the night, for example as airflow changes between each nasal passage, the dilator system may alternate its response to match the required dilation on either side of the nose to maintain a variable therapy during the treatment session.

Yet a further embodiment includes the ability to detect flexure and/or tension in the strips and actively control tension and therefore nasal dilation. Many known detectors 52 are suitable for this purpose.

The above description provides an inexpensive, comfortable and effective nasal dilator. With the mask arrangements, the reduction in resistance of the nasal passage results in improved compliance while using CPAP devices. Additionally, a reduction in resistance results in lower pressure requirements to effectively treat the patient. Consequently, the patient will benefit from a decrease in nasal irritation and dryness.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the invention.

The invention claimed is:

1. A mask to provide continuous positive airway pressure to a patient, the mask comprising:
    a cushion provided to contact the patient's face, and headgear to retain the cushion in contact with the patient's face; and
    a nasal dilator comprising a contact pad attachable to the patient's facial region below each of the patient's eyes and outboard from each side of the patient's nose and a tugging device coupled with each contact pad, the tugging device urging each contact pad in a direction away from the patient's nose,
    wherein the tugging device comprises outward biased U-shaped spring, each contact pad being secured to opposite ends of the spring,
    wherein the nasal dilator is attached to at least part of the cushion or headgear, and
    wherein each contact pad comprises a friction surface on a side thereof facing the patient, and wherein at least part of the headgear is adapted to fit over the spring on the patient's face.

2. A mask according to claim 1, wherein each contact pad comprises one of an adhesive, a self-adhesive tape, and/or a friction surface on a side thereof facing the patient.

3. A mask according to claim 1, wherein each contact pad is formed of a gel material.

4. A mask according to claim 1, wherein the tugging device is provided on part of the headgear.

5. A mask according to claim 1, wherein each contact pad comprises a self-adhesive layer on a side thereof facing the user.

6. The mask of claim 1, wherein the spring is adjustable.

7. A mask according to claim 1, wherein the cushion comprises nasal pillows.

8. A nasal dilator system comprising:
    a nasal dilator including a contact pad attachable to a user's face region below the user's eye and outboard from the user's nose, and a tugging device coupled with the contact pad, the tugging device urging the contact pad in a direction away from the user's nose with a force:
    a nasal resistance measuring device;
    a control system receiving output from the nasal resistance measuring device; and
    a force adjustment mechanism communicating with the control system and coupled with the tugging device, the force adjustment mechanism adjusting the force applied by the tugging device based on the output from the nasal resistance measuring device,
    wherein the nasal dilator comprises two contact pads attachable to respective facial regions on either side of the user's nose, wherein the force adjustment mechanism effects independent adjustment of the force on each of the contact pads.

9. A nasal dilator system according to claim 8, wherein the force adjustment mechanism comprises a motor.

10. A nasal dilator system according to claim 8, wherein the force adjustment mechanism effects independent adjustment based on a position of the user.

11. A nasal dilator system according to claim 8, wherein the force adjustment mechanism effects independent adjustment based on the output from the nasal resistance measuring device.

12. A nasal dilator system according to claim 8, wherein the tugging device comprises a strip of flexible material attached at a first end thereof to the contact pad and attached at a second end thereof to a securing device, the securing device being fixable relative to the user such that the flexible strip is placed under tension, wherein the force adjustment mechanism adjusts the tension based on the output from the nasal resistance measuring device.

* * * * *